United States Patent [19]
Shimura et al.

[11] Patent Number: 6,110,108
[45] Date of Patent: Aug. 29, 2000

[54] HOME CARE SYSTEM, CENTER TERMINAL AND PATIENT TERMINAL

[75] Inventors: Takaki Shimura; Satoshi Mori; Keiichi Murakami; Nagaaki Koshino; Minoru Iwata, all of Kawasaki; Takehito Takano; Keiko Nakamura, both of Tokyo; Junichi Koike; Keiichi Takeda, both of Kawasaki, all of Japan

[73] Assignee: Fujitsu Limited, Kawasaki, Japan

[21] Appl. No.: 08/524,574

[22] Filed: Sep. 7, 1995

[30] Foreign Application Priority Data

Sep. 8, 1994 [JP] Japan .................................. 6-214986
Apr. 4, 1995 [JP] Japan .................................. 7-078807

[51] Int. Cl.$^7$ ............................................ A61B 5/02
[52] U.S. Cl. ...................... 600/300; 128/903; 128/904
[58] Field of Search ................. 128/630, 670–77, 128/696, 700, 903–904; 600/300, 483–484, 509, 513

[56] References Cited

U.S. PATENT DOCUMENTS

| | | | |
|---|---|---|---|
| 4,838,275 | 6/1989 | Lee | 128/904 X |
| 5,339,821 | 8/1994 | Fujimoto | 128/904 X |
| 5,462,051 | 10/1995 | Oka et al. | 128/630 |
| 5,544,649 | 8/1996 | David et al. | 128/630 |
| 5,579,378 | 11/1996 | Arlinghaus, Jr. | 128/904 X |

FOREIGN PATENT DOCUMENTS

| | | |
|---|---|---|
| 5-336435 | 6/1993 | Japan . |
| 5-144093 | 12/1993 | Japan . |

*Primary Examiner*—Jeffrey R. Jastrzab
*Assistant Examiner*—Ryan Carter
*Attorney, Agent, or Firm*—Staas & Halsey

[57] ABSTRACT

There is disclosed a home care system in which a center terminal and a patient terminal are detachably connected to each other through communication lines, such as a public telephone line, an ISDN (integrated services digital network), a CATV (cable television), a radio and the like, and further to center terminals and patient terminals which constitute such a home care system. The patient terminal has an urgency transmitter device for transmitting a predetermined urgency code to the center terminal, and the center terminal comprises an urgency receiver device for receiving, while connected to a first patient terminal, the urgency code transmitted from a second patient terminal, and an urgency alarm device for informing of the fact that the urgency code has been received.

6 Claims, 16 Drawing Sheets

| TEL NOS. | PARTY |
|---|---|
| 0 7 8 — 9 3 6 — 1 2 2 1 | HOME CARE CENTER A |

| REG. NO. 0 | 078-936-1221 | Taro Fujitu |
| --- | --- | --- |
| REG. NO. 1 | | |
| | | |

Fig. 7

| RESERVATION DATE | START TIME | END TIME | TEL NO. | NAME | COMMUNICATION MODE |
|---|---|---|---|---|---|
| 1994/08/01 | 13:00 | 13:50 | 078-936-1221 | Taro Fujitu | AUTO COMMUNICATION |
| 1994/08/01 | 14:00 | × | 044-777-1111 | Hanako Fujitu | AUTO DOWNLOAD |

Fig. 9

| CONTENTS OF CHECK | ORDER OF CHECK → QUESTIONS, REHABILITATION CONTENTS, ADVICES | | |
|---|---|---|---|
| | QUESTIONS | REHABILITATION CONTENTS | ADVICES |
| | • NOT FINE ?<br>• ARE YOU LEADING A REGULAR LIFE ?<br>• DO YOU HAVE SUFFICIENT MEALS ? | • UP AND DOWN OF ARMS<br>• SIMPLE WALKING<br>• LANGUAGE TRAINING | • HOW TO TAKE MEDICINE<br>• INTRODUCTION OF REHABILITATION CENTER |

Fig. 12

| PATIENT TERMINAL TEL NOS. | CODEC SCHEMES | LINES |
|---|---|---|
| A₁ | MPEG(ISDN) | ISDN |
| A₂ | H261(ISDN) | ISDN |
| B₁ | APEX(PUBLIC) | PUBLIC COMMUNICATION LINE |
| B₂ | H261(PUBLIC) | PUBLIC COMMUNICATION LINE |
| C | MPEG(CATV) | CATV |
| D | MPEG(B-ISDN) | B-ISDN |

Fig. 17

HOME CARE SYSTEM, CENTER TERMINAL AND PATIENT TERMINAL

BACKGROUND OF THE INVENTION

1. Field of the Invention

The present invention relates to a home care system in which a center terminal and a patient terminal are detachably connected to each other through communication lines, such as a public telephone line, ISDN (integrated services digital network), CATV (cable television), radio and the like, and further to center terminals and patient terminals which constitute such a home care system.

2. Description of the Related Art

Recently, a home care service capable of practicing care such as rehabilitation at home is noticed in view of the fact that national medical expenses are reduced and patient's comfortability has been advanced. And there is made such an attempt that patient's homes and a home care center such as a hospital and a door-to-door nurse station are connected through visual communication lines such as a video telephone line and CATV so that the patient's care is conducted through communications between the home care center and the patients.

However, according to the conventional attempt, the general visual communication terminals are appropriated without any changes, and there are not almost considered a facility of the application of the home care center, a facility of the use of the patient terminals and the like.

In order to push forward with the home care service utilizing the visual communication terminals, there is a need to construct a home care system sufficiently taking into consideration such application of the home care center, a facility of the use of the terminals and the like.

The conventional home care system involves, for example, the following problems.

(1) In the home care system utilizing the general visual communication terminals, even when a call occurs in an emergency from a patient, it is impossible to grasp the state of the patient, if th e center is "busy" on another line.

(2) In the home care system utilizing the general visual communication terminals, it is impossible to automatically access to the patient terminal and to automatically upload data in the patient terminal.

(3) Hitherto, it is a current situation that newcomers learn measures in the care spot from a veteran public health nurse. Consequently, it would be difficult to efficiently educate competent persons who are available in the spot.

(4) In the home care system utilizing the general visual communication terminals, if a patient's room is dark, it would be difficult to clearly see the patient's expression. Further, in the patient terminal, even if it is desired to record an instruction from the home care center, there is frequent such a case that a patient is a person of advanced age or a patient is not familiar with the operation of the equipment, and thus it would be difficult for the patient to perform an operation for recording.

There are made some proposals to solve the above-mentioned problems on the conventional home care system (refer to, for example, Japanese patent application serial No. 144093/1993 and Japanese patent application serial No. 336435/1993). However, there is not yet proposed a satisfactory means of solving the above-mentioned problems.

In view of the foregoing, it is an object to provide a home care system taking into consideration the application of the system and a facility of the use of the terminals, and further center terminals and patient terminals which constitute such a home care system.

SUMMARY OF THE INVENTION

The first home care system according to the present invention, which attains the above-mentioned object, is characterized in that at least one center terminal and patient terminals are disconnectably connected to each other via a communication line through which communications of data including image data are performed. The patient terminal has an urgency transmitting unit transmitting a predetermined urgency code to said center terminal. The center terminal comprises an urgency receiving unit receiving, while connected to a first patient terminal, the urgency code transmitted from a second patient terminal, and an urgency alarm unit informing of the fact that the urgency code has been received.

It is characterized in that the patient terminal in the first home care system has the urgency transmitting unit transmitting a predetermined urgency code to the center terminal.

Further, it is characterized in that the center terminal in the first home care system comprises an urgency receiving means for unit receiving, while connected to a first patient terminal, the urgency code transmitted from a second patient terminal, and an urgency alarm unit informing of the fact that the urgency code has been received.

While the urgency alarm unit is to inform of the fact that the urgency code is received, typically through performing a predetermined display on a display screen, it is acceptable to inform of receipt of the urgency code by means of informing means other than the display on the screen, for example, a voice, turn-on of the lamp, turning on and off a light or the like.

Further, in the first home care system according to the present invention, it is preferable that the urgency transmitting unit and the urgency receiving unit transmit and receive an address code to identify the patient terminal together with a predetermined urgency code, respectively. In addition, the urgency alarm unit has a registration table in which there are registered the address code of the patient and a name for specifying the patient registered in association with the patient terminal in a corresponding relation, patient identification means for referring to the registration table to identify a name for specifying the patient associated with the address code transmitted, and a patient display unit displaying the name for specifying the patient, which is identified by the patient identification unit.

In this aspect, it is characterized in that in the patient terminal the urgency transmitting unit transmits an address code to identify the patient terminal together with a predetermined urgency code.

Further, in this aspect, it is characterized in that in the center terminal the urgency receiving unit receives an address code to identify the patient terminal together with a predetermined urgency code, and the urgency alarm unit has a registration table in which there are registered the address code of the patient and a name for specifying the patient registered in association with the patient terminal in a corresponding relation, patient identification unit referring to the registration table to identify a name for specifying the patient associated with the address code transmitted, and a patient display unit displaying the name for specifying the patient, which is identified by said patient identification means.

While the term "address code" implies typically a telephone number, it is not restricted to the telephone number.

The address code may also imply a subscriber's number in a communication line which couples only the specified subscribers with each other, or an ID number in a communication line involved in a rural network.

Further, while the term "name for specifying the patient" implies typically the patient's name, it is not restricted to the patient's name. Such a name may also imply the patient' nickname, an ID number or the like.

In the first home care system according to the present invention, it is a preferable aspect to arrange the system in such a manner that said patient terminal has a predetermined urgency handler, and the urgency transmitting means unit transmits to said center terminal, in response to an operation of said urgency handler, an urgency code representative of the most urgent situation among a plurality of urgency codes each representative of an associated urgency priority.

Further, in the first home care system according to the present invention, it is also an preferable aspect to arrange the system in such a manner that said patient terminal has an urgency priority deciding unit deciding through a question an urgency priority of connecting said patient terminal with said center terminal, wherein the urgency transmitting unit and said urgency receiving unit transmit and receive an urgency code according to the urgency priority decided by said urgency priority deciding unit, respectively, and wherein said urgency alarm unit informs of the urgency priority according to the received urgency code.

In this aspect, it is characterized in that the patient terminal has an urgency priority deciding unit deciding through a question an urgency priority of connecting said patient terminal with said center terminal, and the urgency transmitting unit transmits an urgency code according to the urgency priority decided by said urgency priority deciding unit.

Further, in this aspect, it is characterized in that in said center terminal the urgency receiving unit receives an urgency code according to the urgency priority decided by said urgency priority deciding unit, and said urgency alarm unit informs of the urgency priority according to the received urgency code.

In this case, it is preferable that said urgency transmitting unit and the urgency receiving unit transmit and receive inquiry data representative of an inquiry result obtained through the question, respectively, and said urgency alarm unit informs of the inquiry result represented by the received inquiry data together with the urgency priority.

Further, in the first home care system according to the present invention, it is preferable that said center terminal has an interruption permission or inhibition instructing unit for instructing as to whether or not said center terminal interrupts communications with the first patient terminal to permit communications with the second patient terminal which transmits the urgency code. And it is also preferable that said center terminal has an another terminal connecting unit connecting the patient terminal transmitted the urgency code with another center terminal.

This another terminal connecting unit may be so designed to connect the patient terminal of concern to another center terminal through an operation by an operator of the center terminal, alternatively to automatically connect the patient terminal of concern to another center terminal in accordance with the urgency priority represented by the priority code, otherwise, independently of the urgency priority represented by the priority code.

The second home care system according to the present invention, which attains the above-mentioned object, is characterized in that at least one center terminal and patient terminals are disconnectably connected to each other via a communication line through which communications of data including image data are performed, center terminal comprises a schedule table in which there are registered desired address codes among address codes each for identifying patients and desired times and dates each for communication with the patient corresponding to the associated address code a schedule registration operating means for registering the address codes and the times and dates into said schedule table, and a line automatic connecting unit for connecting a line with the patient terminal associated with the address code corresponding to the registered time and date, at the time and date registered in the schedule table.

In the second home care system according to the present invention, it is preferable that the patient terminal has a vital sign sensor for measuring a vital sign, and a vital sign memory for storing the vital sign measured by said vital sign sensor, and the center terminal has a vital sign collection unit uploading the vital sign stored in said vital sign memory provided in the patient terminal which has been connected with the center terminal by the line automatic connecting unit.

The vital sign sensor may be ones which serve to grasp a physical condition of the patient, and is not restricted to the specified sensors. Typically, the vital sign sensor implies a tonometer, an electrocardiograph, a pulse measurement instrument, a clinical thermometer and the like.

Further, in the second home care system according to the present invention, it is preferable that said schedule table registers the address codes and the time and date, and in addition a connecting time required since the line is connected with the patient terminal corresponding to the associated address code at the registered time and date up to disconnecting the line, and the schedule registration operating unit serves to register in said schedule table the address codes and the times and dates, and the connecting time as well. The center terminal further comprises a time counting unit counting the time required since said center terminal is connected with the patient terminal by the line automatic connecting unit, and a display unit displaying a remaining time obtained through subtracting the time elapsed measured by said time counting unit from the connecting time involved in the patient terminal connected by said line automatic connecting unit.

The third home care system according to the present invention, which attains the above-mentioned object, is characterized in that at least one center terminal and patient terminals are disconnectably connected to each other via a communication line through which communications of data including image data are performed. The center terminal comprises:

a home care procedure display unit displaying a procedure for a home care of a patient.

In the third home care system according to the present invention, it is preferable that the center terminal has a care procedure altering operation unit for altering the procedure for the home care of the patient displayed on said home care procedure display unit.

The fourth home care system according to the present invention, which attains the above-mentioned object, is characterized in that at least one center terminal and patient terminals are disconnectably connected to each other via a communication line through which communications of data including image data are performed. The center terminal comprises: an audio data input inputting patient data with voice; and an audio data memory for storing the patient data entered through said audio data input unit.

Incidentally, there is no need that the patient data is only the audio data. It is sufficient for the fourth home care system to provide data including the audio data. As the patient data, it is acceptable to include character data, image data and the like other than the audio data.

The fifth home care system according to the present invention, which attains the above-mentioned object, is characterized in that at least one center terminal and patient terminals are disconnectably connected to each other via a communication line through which communications of data including image data are performed, wherein the patient terminal is provided with a room illumination light for illuminating a room in which the patient terminal is disposed, and wherein the center terminal is provided with a light turn-on operating unit turning on the room illumination light installed on the patient terminal.

In the fifth home care system according to the present invention, it is preferable that said patient terminal is provided with a light control unit controlling a light quantity and/or an illumination angle of the room illumination light installed on the patient terminal, and wherein the center terminal is provided with a light control operation unit giving an instruction as to a control of a light quantity and/or an illumination angle of the room illumination light installed on the patient terminal.

The sixth home care system according to the present invention, which attains the above-mentioned object, is characterized in that at least one center terminal and patient terminals are disconnectably connected to each other via a communication line through which communications of data including image data are performed. The patient terminal has a data recording unit recording data including the image data in communication, a calling party identification unit identifying, when the patient terminal is accessed through said communication line, whether or not a calling party is the center terminal and a data recording control unit actuating the data recording unit to record the data on communication when it is discriminated by said calling party identification means that the calling party is the center terminal.

In the first to sixth home care systems according to the present invention, it is preferable that said center terminal has a plurality of types of communication units adapted to perform communications through an associated communication line, and a communication selecting unit storing address codes each for identifying an associated one of the patient terminals and communication unit adapted to perform a communication through a communication line connected to the patient terminal in the corresponding relation, and for selecting the communication unit on the basis of the address code of the patient.

In this case, it is preferable that the center terminal has a plurality of sorts of codecs each for serving to perform encoding and decoding depending on an associated codec scheme among a plurality of sorts of codec schemes, and at least single sort of codec is provided for each of at least part of the communication unit among said plurality of sorts of communication unit.

Further, in this case it is so arranged that the communication selecting unit stores the address codes and the communication unit in the corresponding relation, respectively, and in addition the address codes on the communication means associated with the plurality of sorts of codecs and the encoding circuits in the corresponding relation, respectively, and selects the communication unit on the basis of the address code of the patient to perform the communication with the patient and in addition selects, if the selected communication unit is associated with any of the plurality of sorts of codecs, the codec on the basis of the address code of the patient.

According to the first home care system of the present invention, the patient terminal and the center terminal have urgency transmitting unit for transmitting an urgency code and urgency receiving unit for receiving the urgency code, respectively, and further the center terminal has urgency alarm unit for informing of the fact that the urgency code has been received. This feature makes it possible for a person in charge of the home care center to know the fact that the urgency code is transmitted, even during the conversation with other patient.

In the first home care system of the present invention, if it is so arranged that for example, the name of the patient is displayed, it is possible to immediately identify the patient who sent the urgency code.

In the first home care system according to the present invention, if the system is arranged in such a manner that the patient terminal has a predetermined urgency handler, and the urgency transmitting unit transmits to the center terminal, in response to an operation of the urgency handler, an urgency code representative of the most urgent situation among a plurality of urgency codes each representative of an associated urgency priority, it is possible to immediately make contact with the home care center when the emergency situation occurs.

Further, in the first home care system according to the present invention, if the system is arranged in such a manner that the patient terminal has an urgency priority deciding unit for deciding through a question an urgency priority of connecting said patient terminal with the center terminal, wherein the urgency transmitting unit and the urgency receiving unit transmit and receive an urgency code according to the urgency priority decided by the urgency priority deciding unit, respectively, and wherein the urgency alarm unit informs of the urgency priority according to the received urgency code, it is possible for the center terminal side, for example, in a case where the urgency priority is not so high such that the urgency handler is operated, to compare physical conditions of the patient now on conversation with an urgency priority of the patient who sent the urgency code, thereby deciding countermeasure as to the response to the patient who sent the urgency code. In this case, if the system is arranged in such a manner that the center side can know not only the urgency code but also the question result upon receipt of it at the center side, it is possible to immediately know physical conditions of the patient who sent the urgency code, thereby deciding with greater precise judgement countermeasure as to the response to the patient who sent the urgency code.

Further, in the first home care system according to the present invention, the center terminal has an interruption permission or inhibition instructing unit for instructing as to whether or not the center terminal interrupts communications with the first patient terminal to permit communications with the second patient terminal which transmits the urgency code. This feature makes it possible, when it is decided that the patient who sent the urgency code is to be treated with a higher priority, to immediately have a conversation with the patient of concern without a need of a procedure which will take troublesomeness such that after the conversation with the patient is temporarily terminated (for example, the receiver is replaced) the operator in charge of the center makes contact with the patient who sent the urgency code (for example, calling the patient who sent the urgency code).

Further, in the first home care system according to the present invention, the center terminal has an another terminal connecting unit for connecting the patient terminal transmitted the urgency code with another center terminal. This feature makes it possible to connect the patient terminal transmitted the urgency code with another center terminal depending on the situations such as the instruction of the person in charge of the center, "busy" on another line in the center side, and the lower or higher urgency priority represented by the urgency code transmitted, thereby responding to the patient sent the urgency code without delays.

According to the second home care system of the present invention, the center terminal comprises: a schedule table in which there are registered desired address codes (typically, telephone numbers) among address codes each for identifying patients and desired times and dates each for communication with the patient corresponding to the associated address code; and line automatic connecting unit for connecting a line with the patient terminal associated with the address code corresponding to the registered time and date, at the time and date registered in the schedule table. This feature makes it possible to avoid such a situation that the person in charge of the center forgets to make contact with the patient, thereby reliably and readily implementing the contact with the patient on schedule.

In the second home care system according to the present invention, the patient terminal has a vital sign sensor (e.g. a tonometer, an electrocardiograph) for measuring vital signs, and a vital sign memory for storing the vital signs measured by the vital sign sensor, and the center terminal has a vital sign collection unit for uploading the vital signs stored in the vital sign memory provided in the patient terminal which has been connected with the center terminal by the line automatic connecting means. This feature makes it possible to automatically collect and accumulate the vital sign measurement data of the patient.

Further, in the second home care system according to the present invention, the schedule table registers the address codes and the time and date, and in addition a connecting time required since the line is connected with the patient terminal corresponding to the associated address code at the registered time and date up to disconnecting the line, and the schedule registration operating unit serves to register in the schedule table the address codes and the times and dates, and the connecting time as well; and the center terminal further comprises a time counting unit for counting the time required since the center terminal is connected with the patient terminal by the line automatic connecting unit, and a display unit for displaying a remaining time obtained through subtracting the time elapsed measured by the time counting unit from the connecting time involved in the patient terminal connected by the line automatic connecting unit. This feature makes it possible for the person in charge of the center to have an efficient conversation with the patient without uselessness, thereby facilitating behavior of the person in charge according to his schedule.

According to the third home care system of the present invention, the center terminal has a home care procedure display unit for displaying a procedure for a home care of a patient. This feature makes it possible even for a newcomer in charge of the center to give an adequate instruction for a home care to the patient.

In the third home care system according to the present invention, the center terminal has also a care procedure altering operation means for altering the procedure for the home care of the patient displayed on the home care procedure display means. This feature makes it possible for the center to customize the care procedure thereby facilitating guidance as to a way of the care suitable for each individual patient or guidance as to a way of the care according to the fashion of the center.

According to the fourth home care system of the present invention, the center terminal has: an audio data input unit for inputting patient data with voice; and an audio data memory for storing the patient data entered through the audio data input unit. This feature makes it possible to promptly input the patient data and in addition to add to the patient data delicate nuances of the care which would be difficult to be expressed with only the character input.

According to the fifth home care system of the present invention, the patient terminal is provided with a room illumination light for illuminating a room in which the patient terminal is disposed, and the center terminal is provided with a light turn-on operating unit for turning on the room illumination light installed on the patient terminal. This feature makes it possible to sufficiently observe the patient even in a case where the illumination of a living room of the patient is insufficient for a camera. Further, in a case where there is a need to urgently know how things stand on the patient, even if the living room of the patient is dark, it is possible to know how things stand in the living room of the patient. Further, in the fifth home care system according to the present invention, the patient terminal is provided with a light control unit for controlling a light quantity and/or an illumination angle of the room illumination light installed on the patient terminal, and the center terminal is provided with a light control operation unit for giving an instruction as to a control of a light quantity and/or an illumination angle of the room illumination light installed on the patient terminal. This feature makes it possible to more clearly grasp how things stand in the living room of the patient.

According to the sixth home care system of the present invention, the patient terminal has: data recording means for recording data including the image data in communication; calling party identification unit for identifying, when the patient terminal is accessed through the communication line, whether or not a calling party is the center terminal; and data recording control unit for actuating the data recording unit to record the data on communication when it is discriminated by the calling party identification unit that the calling party is the center terminal. This feature makes it possible to perform a data recording without a necessity for a recording operation by the patient, and the patient may review the instructions given by the care center.

By the way, according to the conventional home care system, a center terminal and one or more patient terminals are connected through only one communication network. An image quality of the image communication depends on capacity or efficiency of the communication network. This is the similar as to the matter of the costs (including device cost, communication cost, installation cost and the like). On the other hand, clinically, there is no need to always provide the best quality of image to all the patients. It is preferable to select the optimum care excellent in cost performance according to a degree of illness or the like. Further, there is a general opinion such that communication networks have to be integrated and codec systems also have to be standardized. However, in view of the fact that the home care system is a locally closed system and is basically of a star-shaped network of communication between the center terminal and the patient terminals, there is no need to hold fast on the general opinion.

In this respect, according to the present invention, adoption of a plurality of sorts of communication units, adoption of the codecs according to the communication unit, selection of the communication unit based on an address code of the patient terminal of concern, or adoption of communication selecting unit for selecting the codec regarding the communication unit each corresponding to the associated one of the plurality of codecs, permits selection of the patient terminal suitable for the patient, thereby performing communications with the communication network and the codec scheme suitable for the patient terminal between the center terminal and the patient terminal. Therefore, the center terminal may provide a flexible service without holding fast on a single communication network and codec schemes. Thus, it is possible to provide a home care system excellent in cost-performance.

BRIEF DESCRIPTION OF THE DRAWINGS

FIG. 7 is an illustration of a telephone number and patient name registration table at a home care center terminal;

FIG. 9 is an illustration of an example of a scheduler registration table at a home care center terminal;

FIG. 12 is an illustration of an example of a care procedure check list;

FIG. 17 is an illustration of a port switching table provided within a port switching circuit 160 shown in FIG. 16.

DESCRIPTION OF THE PREFERRED EMBODIMENTS

Hereinafter, there will be described embodiments of the present invention.

Figure 1:
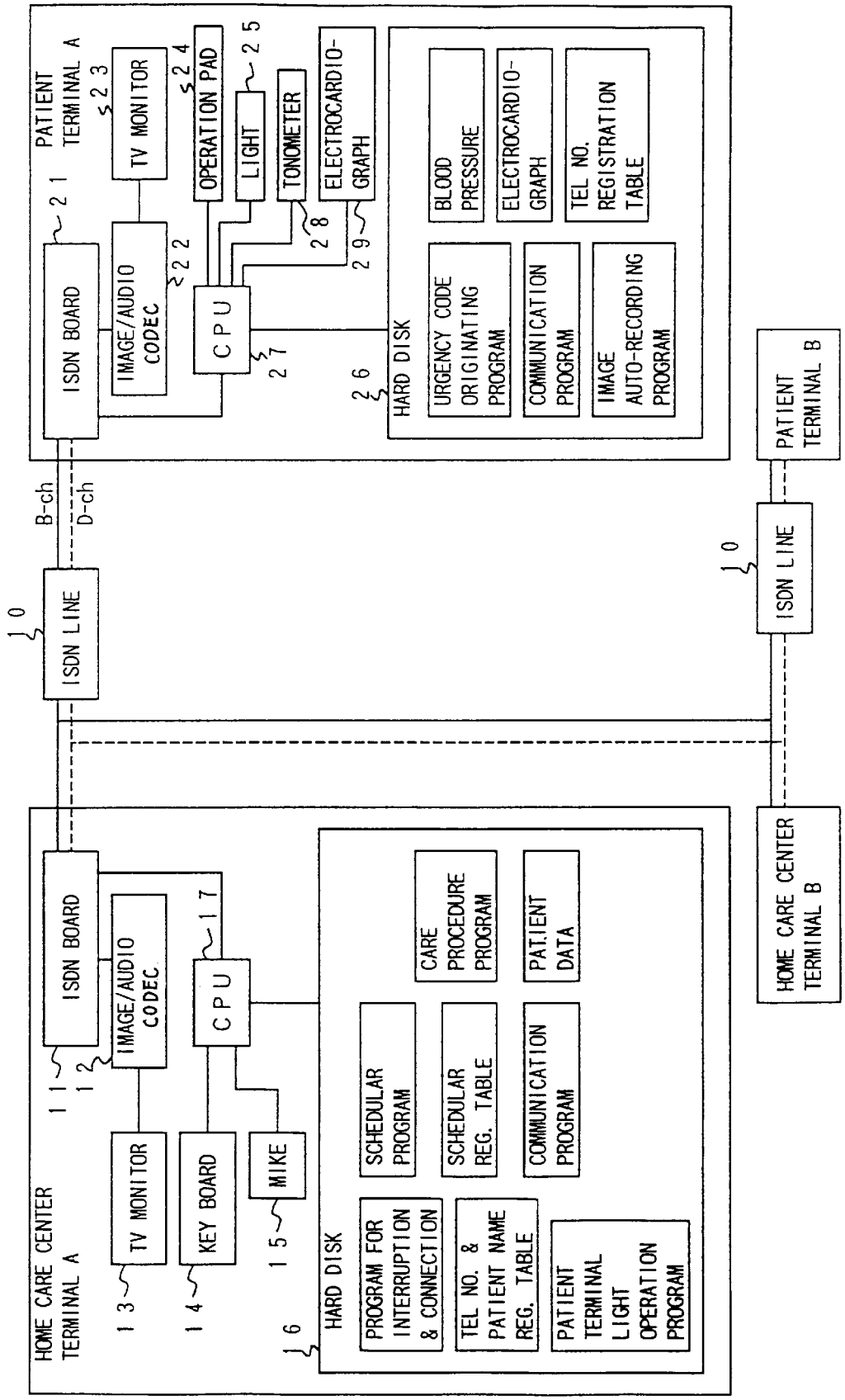
FIG. 1 is a schematic diagram showing an embodiment of a home care system according to the present invention.

FIG. 1 is a schematic diagram showing an embodiment of a home care system according to the present invention.

A home care center terminal is installed at a home care center such as a hospital, a door-to-door nurse station and the like. On the other hand, a patient terminal is installed at a patient's home wherein a patient has, for example, a rehabilitation.

It is acceptable that there are a plurality of home care centers, but not restricted to a single center. It is assumed that each of the home care centers (two) is provided with an associated home care center terminal (A,B).

With respect to the patient terminals, usually, there are provided a lot of sets corresponding to a number of patients each for a patient's home one by one. However, in the present embodiment, to simplify the explanation, it is assumed that there are set two patient terminals A and B to homes of two patients A and B, respectively. Further, it is assumed that two patients A and B usually get guidance of the home care center at which the home care center terminal A is installed.

Two home care center terminals A and B and two patient terminals A and B are connected to each other through ISDN lines 10. Two home care center terminals A and B have each the same structure. In FIG. 1, there is shown details of the structure as to only the home care center terminal A. Similarly, two patient terminals A and B have each the same structure, and thus in FIG. 1, there is shown details of the structure as to only the patient terminal A.

The home care center terminal A comprises an ISDN board 11 for connection of an ISDN line, an image/audio CODEC 12 for compressing image data and audio data to be transmitted into ones adapted for the ISDN line and for expanding received image data and audio data, a television monitor 13, a keyboard 14, a microphone 15 for audio data input, a hard disk 16 for storing various kinds of programs and data, and a CPU 17 for executing a program and performing various kinds of controls.

The patient terminal A comprises an ISDN board 21, an image/audio CODEC 22, a television monitor 23, a hard disk 26 and a CPU 27, an operation pad 24 for operation by a patient, a light 25 for illumination of a patient's living room at which the patient terminal A is installed, a sphygmomanometer 28 and an electrocardiograph 29.

Communications through the ISDN lines 10 are controlled by the CPUs 17 and 27 through execution of communication programs stored in the hard disks 16 and 26. Since the ISDN line and the usual communication itself using the ISDN line are well known, there will be omitted explanations as to the ISDN line 10, the ISDN boards 11 and 21, the image/audio CODECs 12 and 22, the communication programs and the like.

Figures 2, 3:
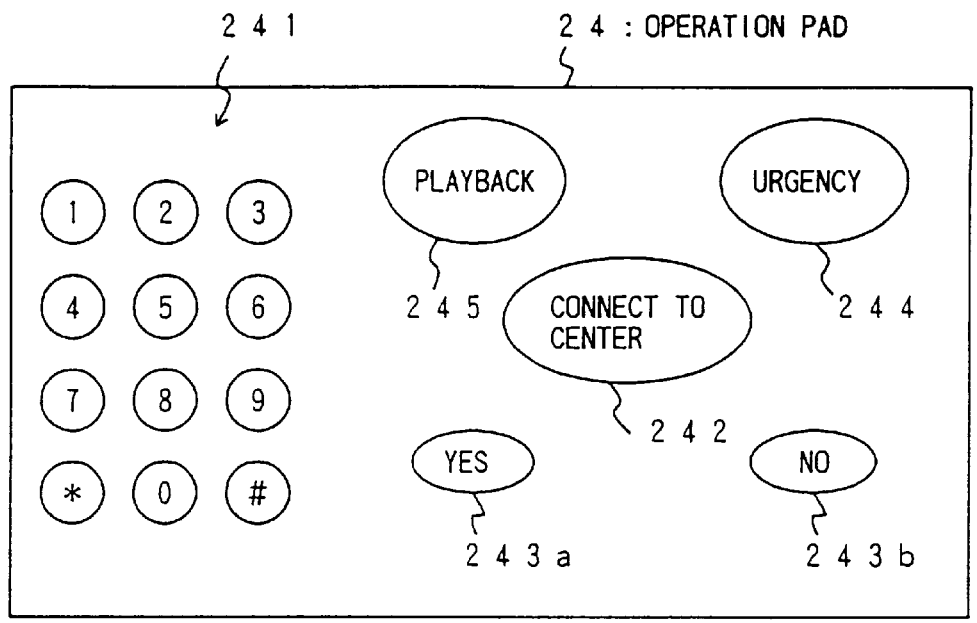
FIG. 2 is an illustration of a key arrangement of an operation pad installed at a patient terminal.
FIG. 3 is an illustration of a telephone number registration table at a patient terminal.

FIG. 2 is an illustration of a key arrangement of an operation pad installed at a patient terminal.

In FIG. 2, an ellipse stands for a push button. The operation pad 24 is equipped with dial keys 241 to which numerals 0–9, and marks * and # are appended, a center connecting push button 242 for connection to the home care center A, "yes" input push button 243a and "no" input push button 243b for inputting answers "yes" and "no" to the inquiry (described later), respectively, an urgency button 244 which is to be pushed when an emergency situation occurs, and a playback push button 245 which is to be pushed when it is desired to regenerate the communication image recorded at the patient terminal.

When making a usual telephone call to one's friends or the like, a person takes the telephone receiver (not illustrated) off the hook to push the telephone number of the destination through the dial keys 241. This permits the person have a usual telephone conversation.

A patient terminal A registers at least a telephone number of the home care center terminal A. Of course, it is acceptable for the patient terminal A to register additionally telephone numbers and abbreviated dialing numbers of one's friends, acquaintances and the like. Here, there will be explained only the communication with the home care center.

Figure 4:
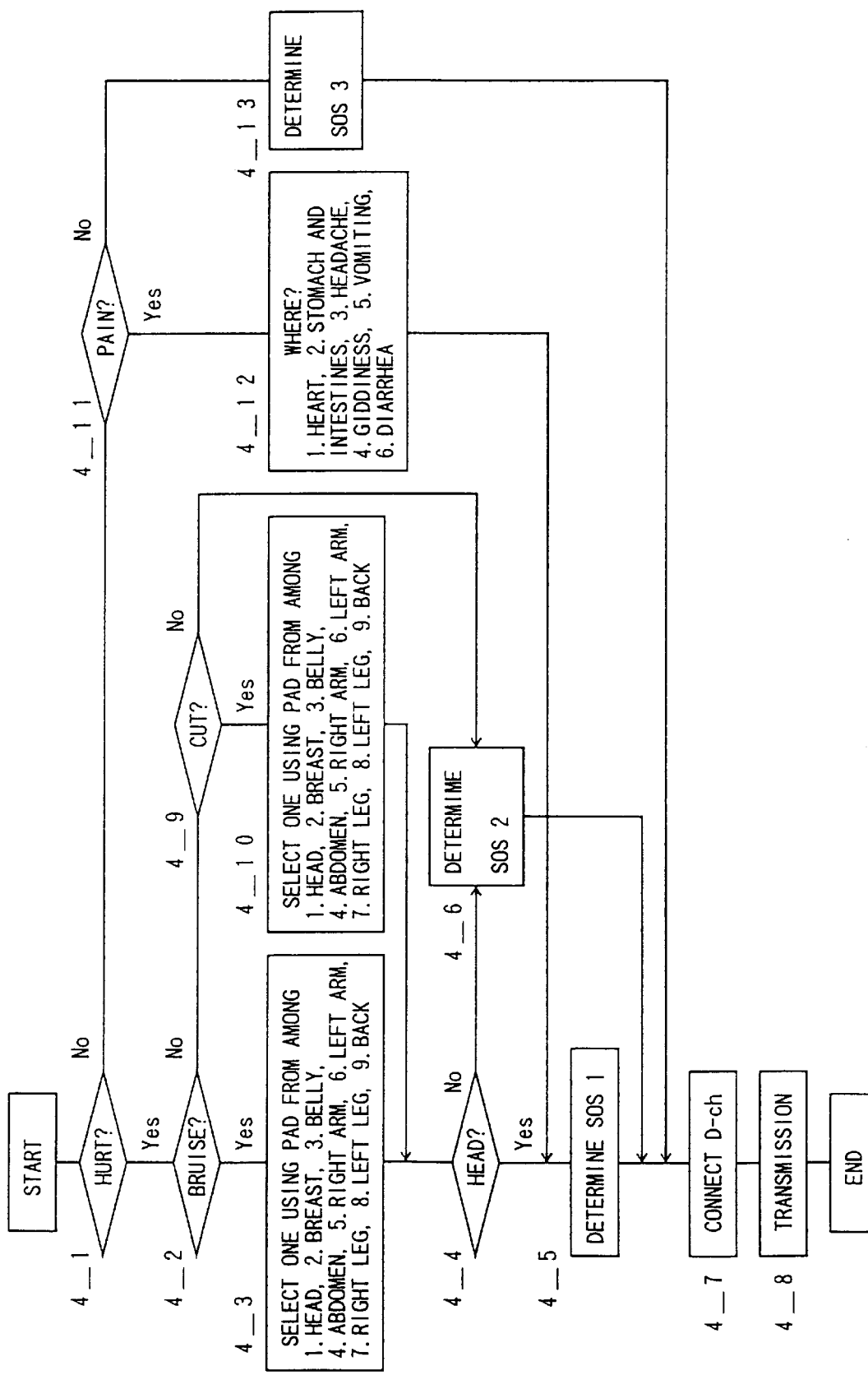
FIG. 4 is a flowchart of an urgency code originating program to be executed at a patient terminal.

FIG. 4 is a flowchart of an urgency code originating program to be executed by the CPU 27 of the patient terminal A when the center connecting push button 242 shown in FIG. 2 is depressed.

When the patient A wishes to communicate with the home care center A, usually, it is implemented through depression of the dial keys 241. However, when the patient determines it is somewhat urgent, the center connecting push button 242 may be depressed so as to execute the program shown in FIG. 4.

First, in step 4_1, the television monitor 23 displays an inquiry as to whether you get hurt. If so, the "yes" input push button 243a on the operation pad 24 is depressed. Thus, the process goes to step step 4_2 in which the television monitor 23 displays an inquiry as to whether you get a bruise. If so, the "yes" input push button 243a is again depressed. Thus, the process goes to step 4_3 in which the television monitor 23 displays a table providing a corresponding relation between numbers and sites of the human body. An operator depresses the associated number key of the dial keys 241. The CPU 27 determines as to whether the operator gets hurt on the head (step 4_4). When it is determined that the operator gets hurt on the head, it is decided that the urgency code to be transmitted is SOS1, and the transmitted data is generated (step 4_5). On the other hand, when it is determined that the operator gets hurt on the portions other than the head, it is decided that the urgency code to be transmitted is SOS2, and the transmitted data is generated (step 4_6). The transmitted data including the urgency code is transmitted through a D-channel of the ISDN line 10 (step 4_7) to the home care center terminal A.

Specifically, it is noted that higher priority of urgency is given for an urgency code provided with younger number subsequent to the symbol mark "SOS". Hence, now to compare the urgency code SOS1 with the urgency code SOS2, the the urgency code SOS1 is of higher priority of urgency.

Figure 5:
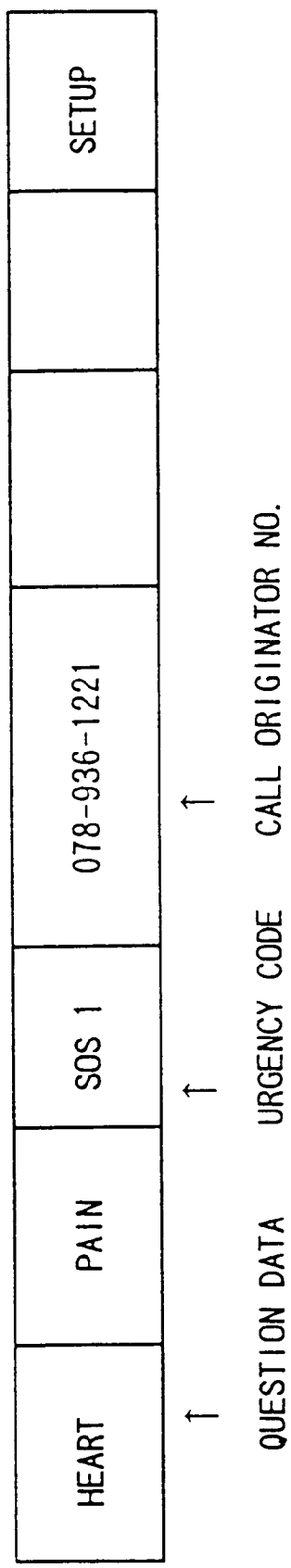
FIG. 5 is an illustration of an example of transmitted data toward a home care center terminal.

FIG. 5 is an illustration of an example of transmitted data toward the home care center terminal A.

This transmitted data include set up data SETUP to decide a transmitted protocol, a telephone number of a call originator (patient terminal A), an urgency code, and question data obtained by questions in the program shown in FIG. 4.

Returning to FIG. 4, the explanation will be continued.

In step 4-2, if the "no" input push button 243b is depressed, the process goes to step 4_9 in which the television monitor 23 displays an inquiry as to whether it is a cut. If so, the "yes" input push button 243a is depressed. Then the process goes to step step 4_10 in which the television monitor 23 displays the table providing a corresponding relation between numbers and sites of the human body, in a similar fashion to that of step 4_3. Thus, the operator depresses the associated number key of the dial keys 241 of the operation pad 24. Thereafter, the process goes to step 4_4. In step 4_9, if the "no" input push button 243b is depressed, the process goes to step 4_6 in which the urgency code SOS2 is determined and the transmitted data is generated.

In step 4_1, if the "no" input push button 243b is depressed, the process goes to step 4_11 in which the television monitor 23 displays an inquiry as to whether you have a pain in your body. If so, the "yes" input push button 243a is depressed. Then the process goes to step 4_12 in which the television monitor 23 displays as to where you have a pain in your body. Thus, the operator depresses the associated number key of the dial keys 241 of the operation pad 24. In this case, anyhow, the process goes to step 4_5 in which the urgency code SOS1 is determined. On the other hand, as will be described later in conjunction with FIG. 5, information involved in step 4_11 is used as question data which are transmitted together with the urgency code.

In step 4_11, if the "no" input push button 243b is depressed, the process goes to step 4_13 in which the urgency code SOS3 is determined, and then the process goes to step 4_7.

Incidentally, when the urgency button 244 of the operation pad 24 shown in FIG. 2 is depressed, the highest priority of urgency code SOS0 is determined and immediately transmitted to the home care center terminal A.

Figure 6:
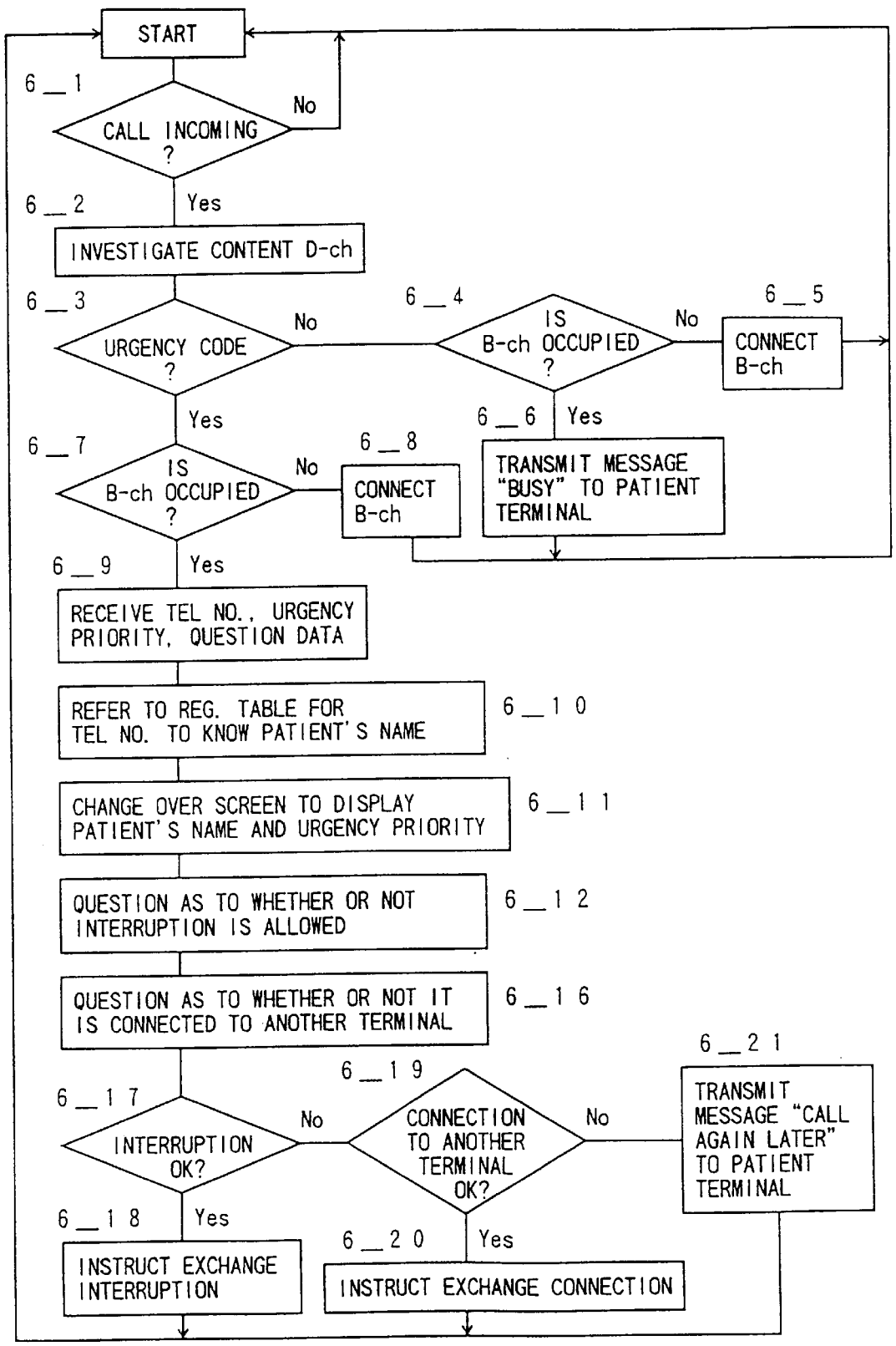
FIG. 6 is a flowchart of an interrupting and connecting program to be executed at a home care center terminal.

FIG. 6 is a flowchart of an interrupting and connecting program to be executed in the CPU 17 of the home care center terminal A.

In step 6_1, it is monitored as to whether call incoming is present. In case of the absence of call incoming, waiting until call incoming occurs. When call incoming occurs, the content of the D-channel of the ISDN line 10 is examined (step 6_2) to check as to whether the urgency code exists in the transmitted data (step 6_3). If no urgency code exists, the process goes to step 6_4 in which it is examined as to whether the B-channel is now occupied. If the B-channel is not occupied, the B-channel is connected thereto (step 6_5). On the other hand, if the B-channel is occupied, a message indicating "busy" is transmitted to the patient terminal of concern (step 6_6).

In step 6_3, when it is recognized that an urgency code is present in the transmitted data through the D-channel, the process goes to step 6_7 in which it is examined as to whether the B-channel is now occupied. If the B-channel is not occupied, the B-channel is connected thereto (step 6_8). On the other hand, if the B-channel is occupied or "busy", the process goes to step 6_9 in which a patient's telephone number, a urgency priority and question data, which are transmitted via the D-channel, are received (refer to FIG. 5). In step 6_10, a patient name registration table is referred to for the patient's telephone number to identify the patient's name of concern.

Figure 7:
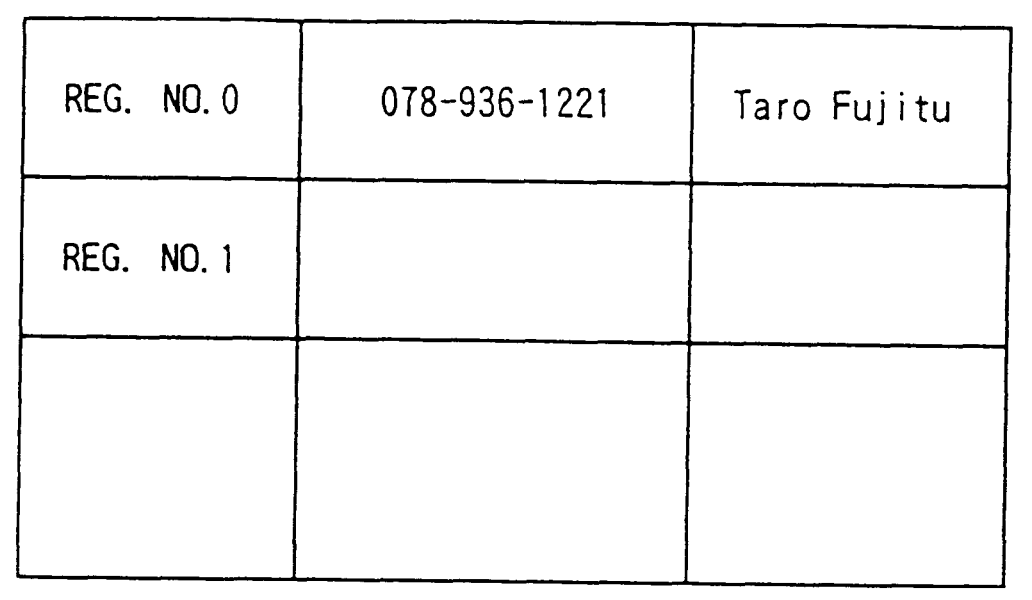

FIG. 7 is an illustration of a telephone number and patient name registration table at the home care center terminal A.

In this table, there are registered a patient name and a telephone number of the patient terminal set to the patient's home in their corresponding relation.

In step 6_10 of the program shown in FIG. 6, this registration table is referred to so as to identify the patient who transmitted the urgency code.

In step 6_11, a screen now on "busy" is interrupted to be changed over to a display screen for data sent out from the patient terminal transmitted the urgency code. In step 6_12, there is added on the display screen a question as to whether the interruption of this patient is allowed. In step 6_13, there is added on the display screen a question as to whether this patient terminal is connected to another home care center terminal.

Figure 8:
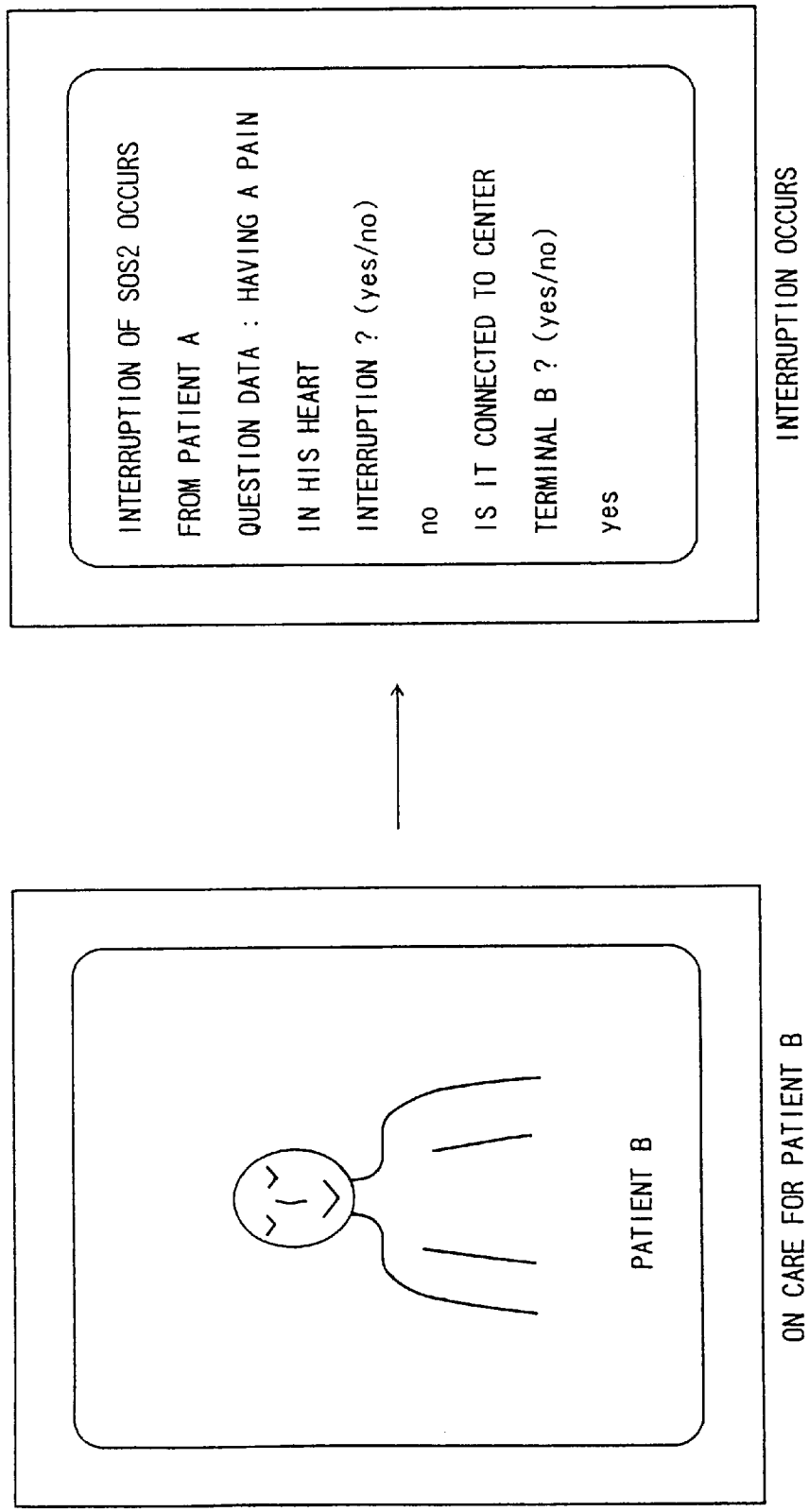
FIGS. 8(A) and 8(B) are illustrations of screens before and after the change over, respectively.

FIGS. 8(A) and 8(B) are illustrations of screens before and after the change over, respectively;

It is assumed that a patient A transmits the urgency code in the middle of the guidance on the home care of the patient B through a conversation with a patient B (FIG. 8(A)). In this case, the display screen shown in FIG. 8(A) is changed over to the display screen shown in FIG. 8(B) on which displayed are a massage (FIG. 5) from the patient A received through the D-channel, a question as to whether an interruption of the patient A is allowed, and a question as to whether the patient terminal A is connected to another home care center terminal B.

The person in charge of the care center confirms this display into comparison with the urgency priority of the patient B now on talking to give an instruction through the keyboard 14 (FIG. 1) as to whether an interruption of the patient A is allowed (step 6_17). In a case where an interruption of the patient A is allowed, an interruption instruction is issued to a switching system (step 6_18) so that the person in charge of the care center starts the conversation with the patient A. On the other hand, when it is instructed that an interruption of the patient A is allowed and the patient terminal A is to be connected to another home care center terminal B (step 6_19), there will be issued to the switching system such an instruction that the patient terminal A is connected to another home care center terminal B (step 6_20). Thus, the display screen returns to the screen (FIG. 8(A)) for a conversation with the patient B.

When such an instruction that there is no need to connect the patient terminal A to even another home care center terminal B is issued, a message such that "please call again later" is transmitted to the patient terminal A, and then the conversation with the patient B may be resumed.

FIG. 9 is an illustration of an example of a scheduler registration table at the home care center terminal A.

In the hard disk 16 of the home care center terminal A, there is prepared a scheduler registration table as shown in FIG. 9. A person in charge in the center writes necessary matters into the table through an operation of the keyboard 14.

According to the example shown in FIG. 9, the following matters are written into the table:

(1) To automatically call Mr. Taro Fujitsu, TELEPHONE: 078-936-1221, at 13:00, the first of August, 1994, to speak fifty minutes up to 13:50 to give guidance in the home care and the like; and (2) To automatically call Mrs. Hanako Fujitsu, TELEPHONE: 044-777-1111, at 14:00, the first of August, 1994, to load data as to blood pressure and electrocardiogram on the home care center terminal side.

Figure 10:
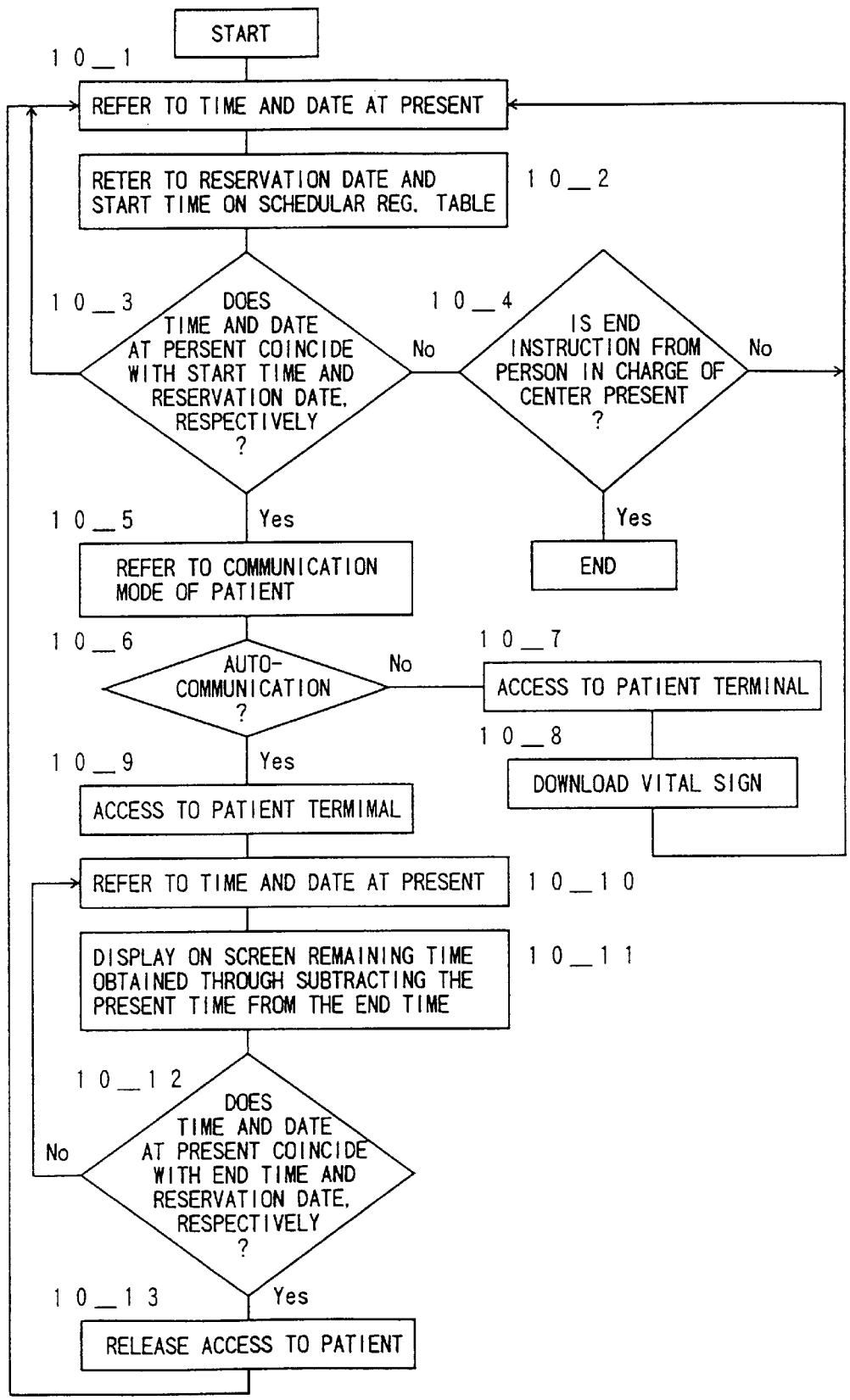
FIG. 10 is a flowchart of a scheduler program to perform a scheduling of communications with patients to be executed at a home care center terminal.

FIG. 10 is a flowchart of a scheduler program to perform a scheduling of communications with patients, which program is stored in the hard disk of the home care center terminal.

This program starts in accordance with an instruction through the keyboard 14 by an person in charge in the care center. Incidentally, it is assumed that the patient terminals A and B are each in a state that the power is always kept on turn-on.

In step 10_1, know the present time and date referring to a timer (not illustrated) which is incorporated into the home care center terminal A. In step 10_2, the reservation date and the starting time on the scheduler registration table as shown in FIG. 9 are referred to. In step 10_3, it is judged as to whether the present time and date coincides with the reservation date and the starting time on the scheduler registration table. If the reservation date and the starting time appearing at any column on the scheduler registration table does not coincide with the present time and date, the process goes to step 10_4 in which when termination instruction is issued from the center, the routine is terminated. On the other hand, if no termination instruction is issued from the center, the program returns to step 10_1 in which the present time and date are again referred to.

In step 10_3, when the reservation date and the starting time appearing at any column in the scheduler registration table coincides with the present time and date, the process goes to step 10_5 in which an item of a communication mode of the associated patient terminal is referred to. In step 10_6, it is judged as to whether the communication mode is concerned with an automatic communication or an automatic download. If it is not concerned with the automatic communication, in other words, it is concerned with the automatic download, the process goes to step 10_7 in which the associated patient terminal is accessed to download the vital signs, that is, in this case, blood pressure and electrocardiogram, on the home care center terminal A (step 10_8). The vital signs thus downloaded are filed on the patient data in the hard disk 16 of the home care center terminal A.

Incidentally, it is assumed that in the patient terminal side, prior to the time of such download, the patient's blood pressure and electrocardiogram are measured using a tonometer 28 and an electrocardiograph 29 (FIG. 1) and those data are stored in the patient terminal.

After the download of the vital signs is executed in step 10_8, the process returns to step 10_1 in which the present time and date are referred to.

In step 10_6, when it is decided that the communication mode is concerned with the automatic communication, the process goes to step 10_9 in which the associated patient terminal is accessed. In step 10_10, the present time and date are again referred to, and the remaining time, which is generated through the subtraction of the current time from the termination time on the associated column in the scheduler registration table, is displayed on the screen. Further, the patient's image now on conversation is also simultaneously displayed on the screen. It is possible for the person in charge of the center to additionally write the condition of the patient and the like into the patient data file through an operation of the keyboard 14 while having the conversation with the patient. The patient data file may store also audio data. Thus, it is possible to store in the patient data file the voice of the person in charge as it is using the microphone 15. In this manner, since the patient data file may store audio data, it is possible to record as the patient data also the fine nuances of care such that it would be difficult to express meaning in writing.

In step 10_12, it is judged as to whether the present time and date coincides with the reservation date and the termination time. Up to the coincidence the present time and date is referred to (step 10_10), and the remaining time is displayed (step 10_11). When the coincidence occurs, the process goes to step 10_13 in which access to the patient is released.

In this manner, a systematic access to the patient is carried out.

Figure 11:
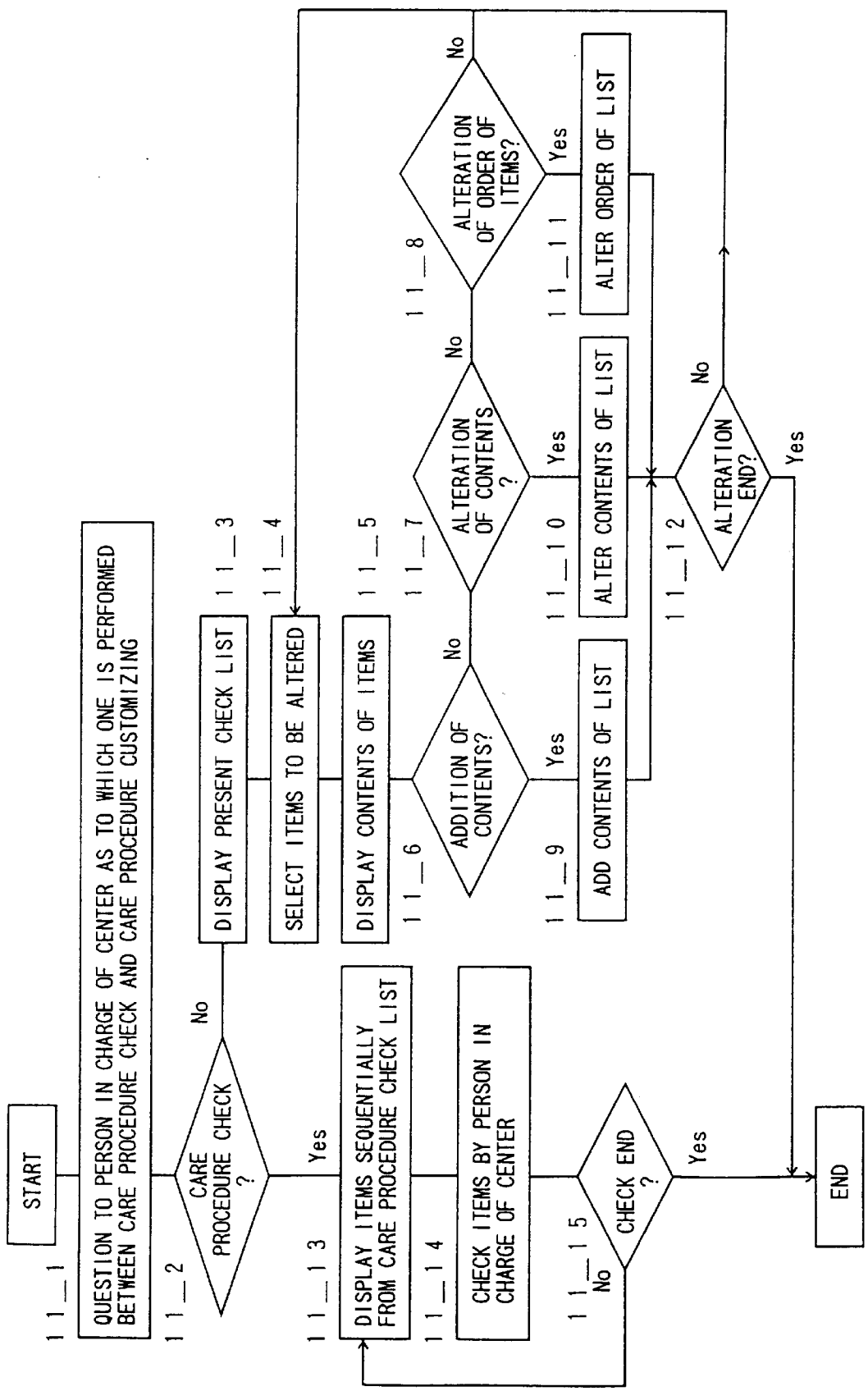
FIG. 11 is a flowchart of a care procedure program to be executed at a home care center terminal.

FIG. 11 is a flowchart of a care procedure program to be executed at a home care center terminal. This program starts through an operation of the keyboard 14 by an operator in charge of the center.

When the program starts through an operation of the keyboard 14 by the operator in charge and the patient is specified, first, in step 11_1, the television monitor 13 displays a question as to which one is performed between "a care procedure check" and "a care procedure customizing".

When the operator in charge answers to the question through an operation of the keyboard, in step 11_2, it is judged as to which one is to be performed between "a care procedure check" and "a care procedure customizing". In case of not "a care procedure check", in other words, in a case where "a care procedure customizing" is to be carried out, the process goes to in step 11_3 in which the television monitor 13 displays items of the present check list of the associated patient.

FIG. 12 is an illustration of an example of a care procedure check list.

In the care procedure check list, there are recorded items "question", "rehabilitation", and "advice", which have been created to meet the care of the associated patient, and their contents.

In step 11_3, the television monitor 13 displays the above-mentioned items of the care procedure check list. In step 11_4, the item which is intended to be altered is selected through an operation of the keyboard. In step 11_5, the content of the item thus selected is displayed on the television monitor 13.

Through the keyboard 14, there is issued an instruction as to the selection among an addition of the listed content, a change of the listed content and an alteration of the order of the list involved in the content, and in addition through an operation of the keyboard, there is inputted an added content or a changed content, otherwise, there is issued an instruction as to the alteration of the order of the list (step 11_6 to step 11_11). The routine is terminated when an instruction of the alteration termination of the check list is made through the keyboard (step 11_12), otherwise a selection of an altered item is again carried out.

In step 11_2, when it is decided that the instruction issued from the person in charge is involved in the care procedure check, the television monitor 13 displays the respective items in the care procedure check list as shown in FIG. 12 and the associated contents, so that the operator in charge checks the contents of the items one by one for each item (step 11_13, 11_14). When the check on a certain item is terminated (it is inputted through an operation of the keyboard), the subsequent item is displayed. When the check on the whole items is terminated, running of this care procedure check program is terminated.

The care procedure check program thus created and/or altered is referred to during giving guidance in the care of the associated patient through the conversation with the patient. Consequently, it is possible even for a newcomer of person in charge to give a sufficient guidance in the care.

Figure 13:
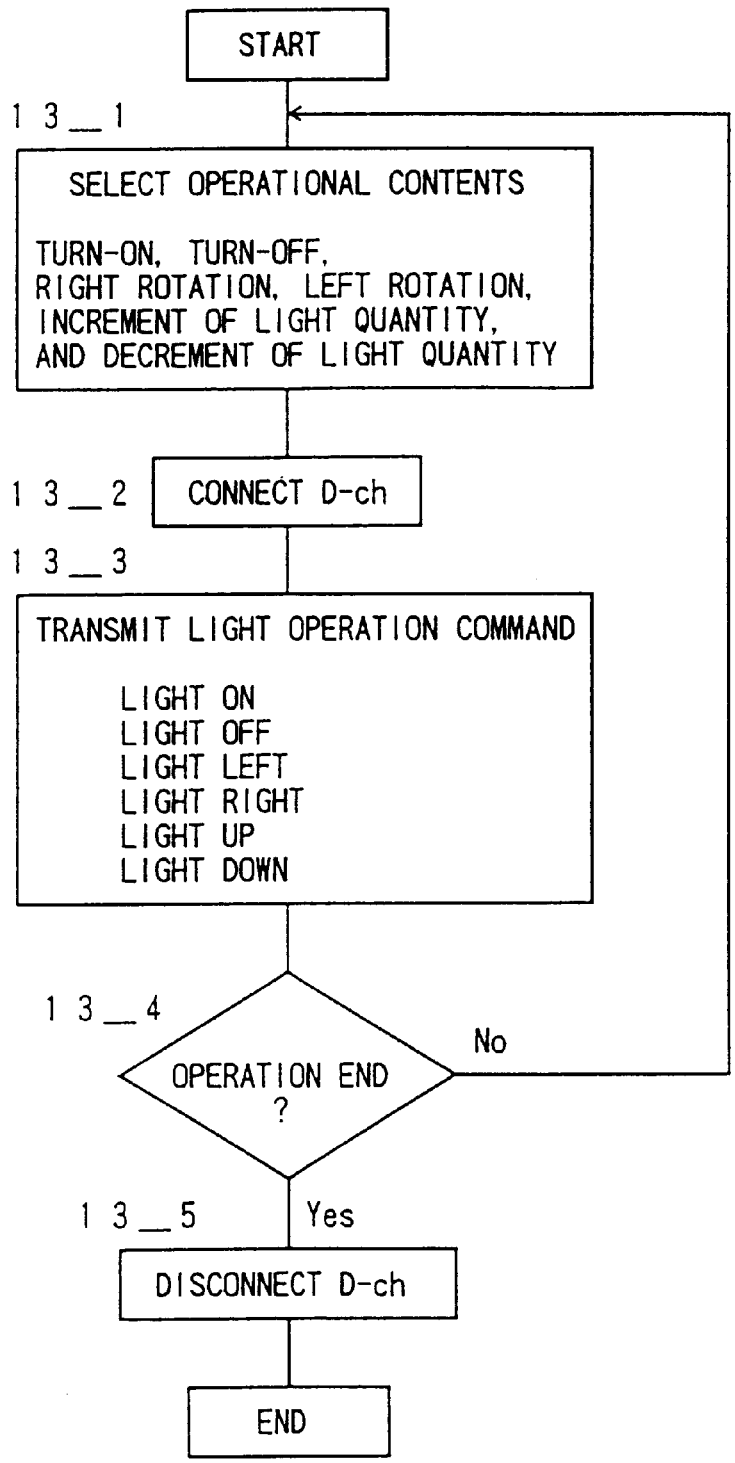
FIG. 13 is a flowchart of a patient terminal light operating program to be executed at a home care center terminal.

FIG. 13 is a flowchart of a patient terminal light operating program to be executed at the home care center terminal.

This program starts through an operation of the keyboard 14 by the person in charge of the center in such a situation that for example, even if the person in charge of the center calls the patient of concern over and over, the patient of concern does not come on the phone, and also even if the person in charge of the center wishes to know through the television monitor 13 how things stand in his room, it is too dark to know how things stand in his room.

In step 13_1, the television monitor 13 displays a list of operational contents, for example, the operational contents of the light 25 (FIG. 1) of the patient terminal, such as a turn-on, a turn-off, a right rotation (turning the light to the right), a left rotation (turning the light to the left), a light quantity increment and a light quantity decrement. A desired one is optionally selected among those operational contents through an operation of the keyboard. When the desired one is selected, the D-channel of the ISDN line 10 is connected to transmit a light operation command according to the selected operational content. The associated patient terminal receives the light operation command, so that the light 25 is controlled in accordance with the received command. When the light operation is terminated, the line of the D-channel is released to terminate this routine (step 13_4, 13_5). In a case where a further operation is desired, the process returns to step 13_1.

In this manner, the television monitor 13 in the care center side displays as to how things stand in the room of patient of concern. Thus, it is possible to know how things stand in his room, thereby confirming the presence or absence of occurrence of an unusual situation.

Figure 14:
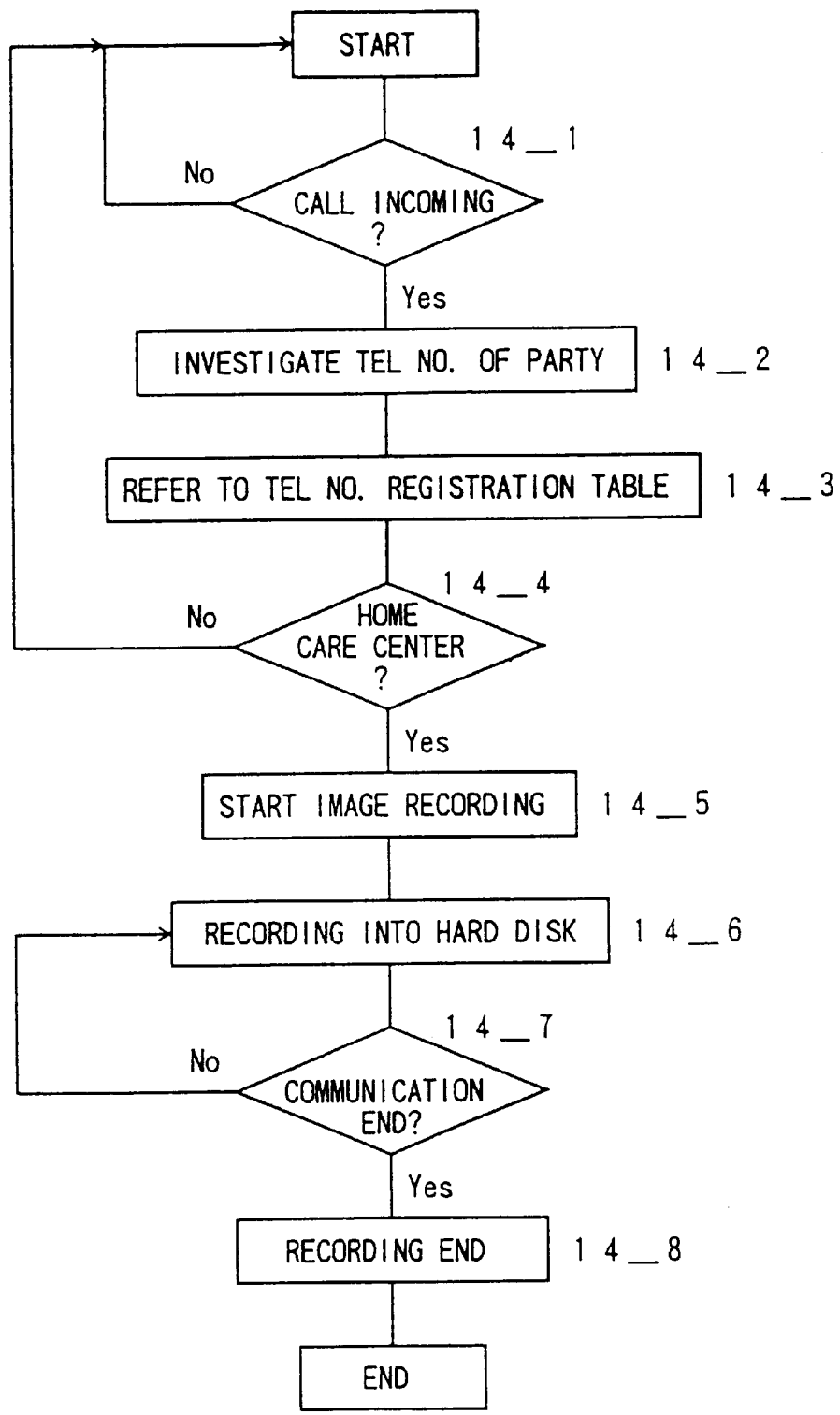
FIG. 14 is a flowchart of a visual automatic recording program to be executed at a patient terminal.

FIG. 14 is a flowchart of a visual automatic recording program to be executed at a patient terminal.

In step 14_1, it is decided as to whether call incoming occurs. If no call incoming occurs, a standby is held until call incoming occurs. When call incoming occurs, the process goes to step 14_2 in which a telephone number of a party in call originating is investigated from data transmitted through the D-channel to refer to a telephone number registration table (FIG. 3)(step 14_3). In step 14_4, it is checked as to whether the party in call originating is a home care center A in charge of the associated patient. When it is not the home care center A in charge, a standby is held until the next call incoming occurs. When it is the home care center A in charge, a recording of images and speeches transmitted from the home care center A in charge is initiated (step 14_5). The images and speeches are recorded on the hard disk until the communication with the home care center A in charge is terminated (step 14_6 to 14_8).

In this manner, when called up from the home care center A in charge, the contents of the communication are automatically recorded. Thus, it is possible for the patient to review the instruction from the care center.

Figure 15:
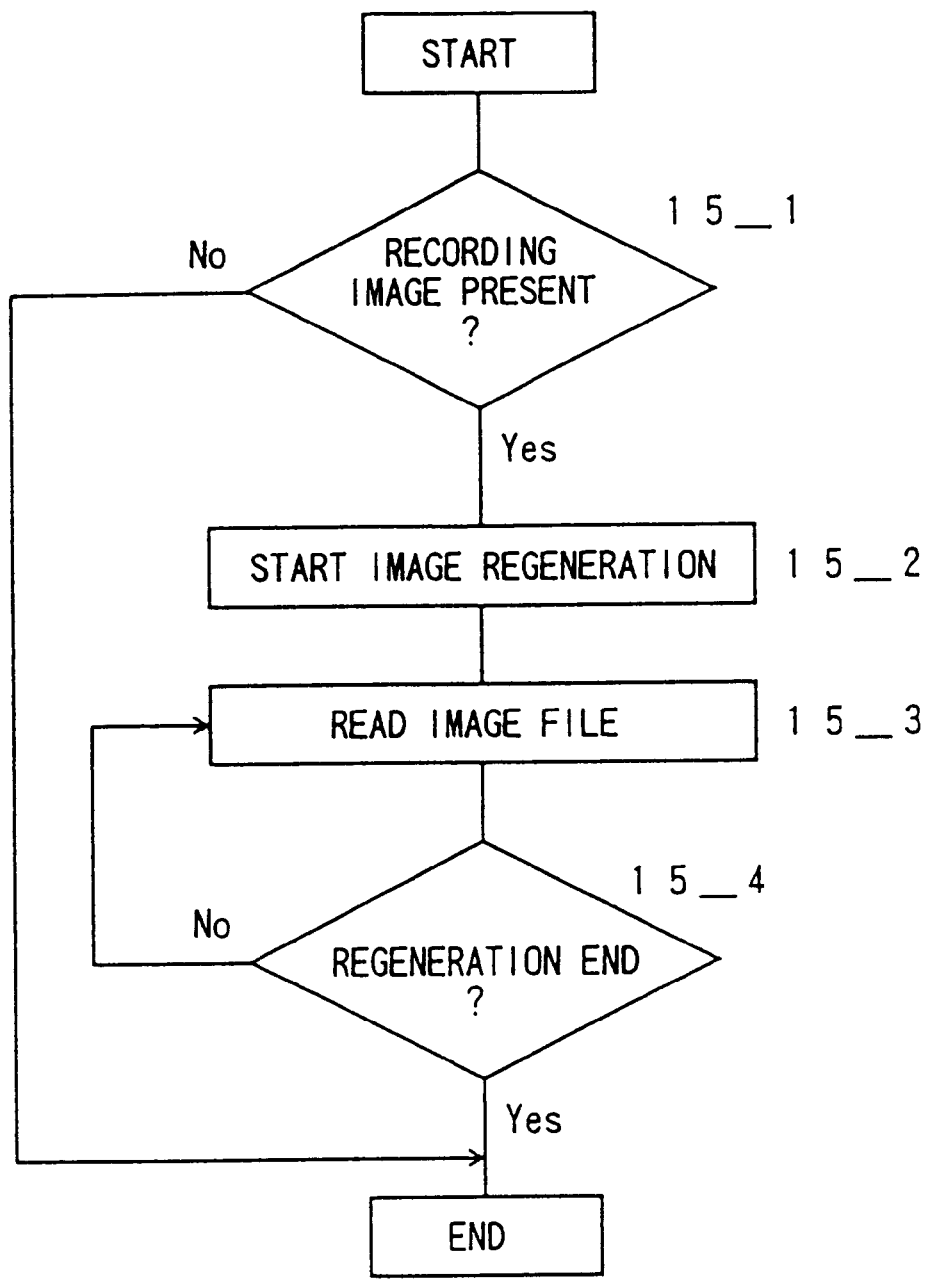
FIG. 15 is a video playback program to be executed at a patient terminal.

FIG. 15 is a video playback program to be executed at a patient terminal.

When the playback push button 245 on the operation pad 24 (FIG. 2) is depressed, this program starts. In step 15_1, it is determined as to whether a recorded image is present. When a recorded image is absent, the routine is terminated. When a recorded image is present, a regeneration of the image is initiated (step 15_2) so that the visual file is sequentially read to display the images on the television monitor 23 (step 15_3, 15_4).

Incidentally, the above-mentioned embodiment is involved in the use of the ISDN line. However, the home care system of the present invention is not restricted to one involved in the use of the ISDN line. It is acceptable, of course, to use a CATV, radio and the like. Further, as will be described hereinafter, it is also acceptable to optionally select anyone of a plurality of communication lines in accordance with a patient terminal into the use.

Figure 16:
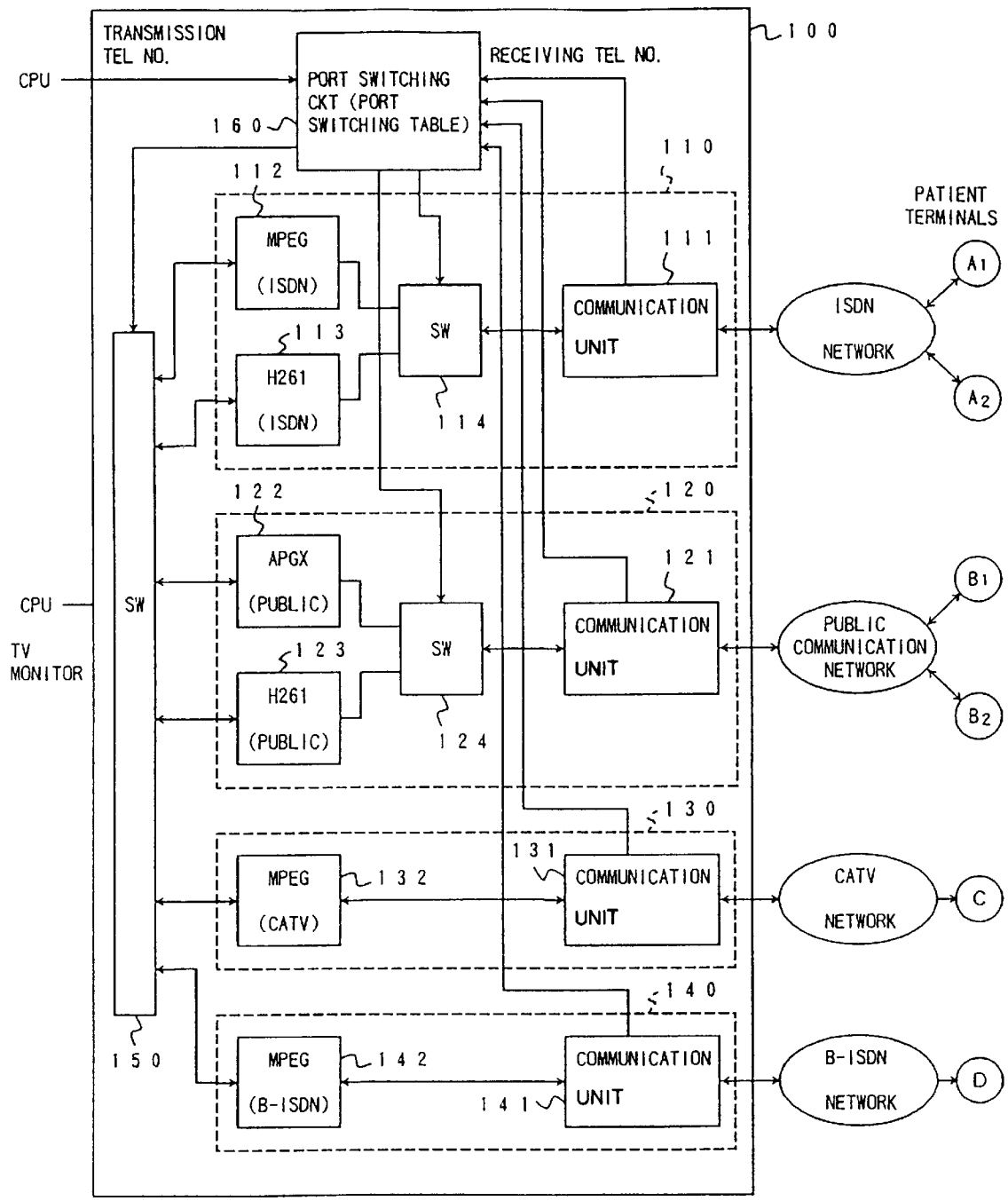
FIG. 16 is a block diagram of part of a care center terminal according to another embodiment different from the embodiment shown in FIG. 1, in the home care system according to the present invention.

FIG. 16 is a block diagram of part of a care center terminal according to another embodiment different from the embodiment shown in FIG. 1, in the home care system according to the present invention.

In FIG. 16, there is shown a data input and output unit 100 corresponding to the ISDN board 11 and the image/audio CODEC 12 in the embodiment shown in FIG. 1.

The data input and output unit 100 constituting a center terminal is connected to a plurality of kinds of communication networks, that is, an ISDN, a public communication network (analog telephone line network), a CATV network, and a B-ISDN. In this system, connected to the ISDN is two patient terminals A1 and A2; to the public communication network is two patient terminals B1 and B2; to the CATV network is a patient terminal C; and to the B-ISDN is a patient terminal D, respectively. The data input and output unit 100 is provided with communication ports 110, 120, 130 and 140 which are connected to the ISDN, the public communication network, the CATV network and the B-ISDN, respectively. Communication unit 111, 121, 131 and 141, which constitute parts of the communication ports 110, 120, 130 and 140, respectively, carry each a communication through the associated communication network. The communication port 110 is provided with an ISDN line-use-MPEG codec 112 which serves to perform coding (including decoding) on the basis of the MPEG standard, and an ISDN line-use-H261 codec 113 which serves to perform encoding and decoding on the basis of the H261 standard. The communication port 120 is provided with a public communication line-use-APEX codec 122 which serves to perform encoding and decoding on the basis of the APEX standard (not International Standard, but a private standard: e.g. MCMJAPAN company standard) and a public communication line-use-H261 codec 123 which serves to perform encoding and decoding on the basis of the H261 standard. The communication ports 130 and 140 are provided with a CATV line-use-MPEG codec 132 which serves to perform encoding and decoding on the basis of the MPEG standard and a B-ISDN line-use-MPEG codec 142 which serves to perform encoding and decoding on the basis of the MPEG standard, respectively.

The communication port 110 is provided with a switch circuit 114 for selectively switchingly connecting the MPEG codec 112 and the H261 codec 113 to the the communication means 111. The communication port 120 is provided with a switch circuit 124 for selectively switchingly connecting the APEX codec 122 and the H261 codec 123 to the the communication unit 121. There is provided a switch circuit 150 between each of the communication ports 110, 120, 130 and 140 and each of the CPU 17 and the television monitor 13 (FIG. 1). Data communication is performed through the switch circuit 150 between each of the ports 110, 120, 130 and 140 and the CPU 17. The respective ports 110, 120, 130 and 140 may transmit data through the switch circuit 150 to the television monitor 13.

The data input and output unit 100 further comprises a port switching circuit 160 having a port switching table.

FIG. 17 is an illustration of a port switching table provided within the port switching circuit 160.

The port switching table shows telephone numbers of patient terminals A1, A2, B1, B2, C and D, codec schemes for the patient terminals A1, A2, B1, B2, C and D, and sort of communication lines to which the patient terminals A1, A2, B1, B2, C and D are connected, respectively, in their corresponding relation. In the table, for the purpose of simplification, the telephone numbers of patient terminals A1, A2, B1, B2, C and D are denoted by the same reference marks as those of the patient terminals.

When the center terminal side calls the patient terminal, the telephone number of the patient terminal is inputted from CPU 17 of the center terminal to the port switching circuit 160. Thus the port switching circuit 160 refers to the port switching table shown in FIG. 17 to control the switch circuit 150 in such a manner that the communication port (communication means) suitable for the patient terminal to be called is selected. When the communication ports 110 or 120 is selected, the port switching circuit 160 also refers to the port switching table shown in FIG. 17 to control the switch circuits 114 or 124 in such a manner that the codec suitable for the patient terminal to be called is selected. In this manner, data communication is performed between the center terminal and the patient terminal through the communication means and the codec which are suitable for the patient terminal as the destination.

On the other hand, when the patient terminal side is on the phone, as seen from FIG. 5, the telephone number of the call originator (patient terminal) is first transmitted. Therefore, upon receipt of the telephone number, the communication means passes the received telephone number to the port switching circuit 160. Thus, the port switching circuit 160 controls necessary ones among the switch circuits 150, 114 and 124 in a similar fashion to that of a case where the center terminal makes a telephone for the patient terminal.

Incidentally, according to the embodiment, the communication port 130 has the MPEG codec 132. However, in a case where the communication is performed with analog NTSC signals which are not encoded, the MPEG codec 132 can be omitted. Further, when the signals encoded according to the MPEG codec scheme and the NTSC signals not encoded are received and transmitted, it may be so arranged that the MPEG codec 132 is provided and when the communication by the NTSC signals is performed, the MPEG codec 132 is bypassed.

Further, according to the explanation as to FIGS. 16 and 17, the data input and output unit 100 of the center terminal is provided with the port switching circuit 160. However, it is noted that the port switching circuit 160 may be substituted by a program executed by the CPU 17 (FIG. 1) and the switching control signals for the switch circuits 150, 114 and 124 are supplied to the data input and output unit 100.

As described above, the home care system according to the present invention and further center terminals and patient terminals, which constitute such a home care system, takes into consideration the application of the system and a facility of the use of the terminals. Thus, according to the present invention, it is possible to provide a system which is excellent in operational efficiency and is effective for a home care.

The present invention is not limited to the particular embodiments described above. Various changes and modifications may be made within the spirit and scope of the invention.

We claim:

1. A home care system comprising:
    patient terminals comprising at least a first patient terminal and a second patient terminal, each of said patient terminals comprising urgency transmitting means for transmitting a predetermined urgency code;
    at least one center terminal comprising:
        urgency receiving means for receiving, while connected to the first patient terminal, the predetermined urgency code transmitted from the second patient terminal,
        urgency alarm means for indicating that the predetermined urgency code has been received, and
        interruption permission or inhibition instructing means for instructing said at least one center terminal whether to interrupt communications with said first patient terminal to permit communications with said second patient terminal which transmitted the predetermined emergency code; and
    a communication line disconnectably connecting the at least one center terminal and the patient terminals to each other, said communication line transmitting communications of data including image data, wherein each of said patient terminals further comprises urgency priority deciding means for deciding through a question an urgency priority of connecting said each of said patient terminals with said at least one center terminal, wherein said urgency transmitting means and said urgency receiving means transmit and receive an urgency code according to the urgency priority decided by said urgency priority deciding means, respectively, and wherein said urgency alarm means informs of urgency priority according to the received urgency code.

2. A system according to claim 1, wherein said at least one center terminal further comprises:

a plurality of types of communication means each adapted to perform communications through an associated communication line, and communication selecting means for storing address codes each for identifying an associated one of the patient terminals and communication means adapted to perform a communication through a communication line connected to the associated one of the patient terminals in a corresponding relation, and for selecting the communication means on the basis of the address code of a patient.

3. A system according to claim 2, wherein said at least one center terminal further comprises a plurality of types of codecs each performing one of an encoding and a decoding depending on an associated codec scheme among a plurality of codec schemes, and at least one type of codec being provided for each of at least part of the communication means among said plurality of types of communication means.

4. A system according to claim 3, wherein said communication selecting means stores the address codes and the communication means in a corresponding relation, respectively, and in addition the address codes of the communication means associated with the plurality of types of codecs and the codecs in a corresponding relation, respectively, and selects the communication means on the basis of the address code of the patient to communicate with the patient and in addition selects, if the selected communication means is associated with any of the plurality of types of codecs, the codec on the basis of the address code of the patient.

5. A center terminal in a home care system in which at least one center terminal and patient terminals are disconnectably connected to each other via a communication line through which data communications including image data are performed, said center terminal comprising:

urgency receiving means for receiving, while connected to a first patient terminal, an urgency code transmitted from a second patient terminal;

urgency alarm means for indicating that the urgency code has been received; and interruption permission or inhibition instructing means for instructing said center terminal whether to interrupt communications with the first patient terminal to permit communications with the second patient terminal which transmitted the urgency code, wherein each of said patient terminals further comprises urgency priority deciding means for deciding through a question an urgency priority of connecting said each of said patient terminals with said center terminal, wherein said patient terminals and said center terminal transmit and receive an urgency code according to the urgency priority decided by said urgency priority deciding means, respectively, and wherein said urgency alarm means informs of urgency priority according to the received urgency code.

6. A home care system comprising:

patient terminals comprising at least a first patient terminal and a second patient terminal, each of said patient terminals comprising an urgency transmitting unit transmitting a predetermined urgency code;

at least once center terminal comprising:

an urgency receiving unit receiving, while connected to the first patient terminal, the predetermined urgency code transmitted from the second patient terminal, an urgency alarm unit indicating that the predetermined urgency code has been received, and an interruption permission or inhibition instructing unit instructing said at least one center terminal whether to interrupt communications with said first patient terminal to permit communications with said second patient terminal which transmitted the predetermined emergency code; and a communication line connecting the at least one center terminal and the patient terminals to each other, said communication line transmitting communications of data including image data and allowing the at least one center terminal and the patient terminals to be disconnected from each other, wherein each of said patient terminals further comprises urgency priority deciding means for deciding through a question an urgency priority of connecting said each of said patient terminals with said at least one center terminal, wherein said urgency transmitting means and said urgency receiving means transmit and receive an urgency code according to the urgency priority decided by said urgency priority deciding means, respectively, and wherein said urgency alarm means informs of urgency priority according to the received urgency code.

* * * * *